United States Patent

Runeman et al.

Patent Number: 5,486,168
Date of Patent: Jan. 23, 1996

[54] INCONTINENCE GUARD FOR MEN

[75] Inventors: Bo Runeman, Partille; Peter Rönnberg, Mölndal, both of Sweden

[73] Assignee: Molnlycke AB, Gothenburg, Sweden

[21] Appl. No.: 354,805

[22] Filed: Dec. 13, 1994

Related U.S. Application Data

[63] Continuation of Ser. No. 855,042, filed as PCT/SE90/00744, Nov. 16, 1990, abandoned.

[30] Foreign Application Priority Data

Nov. 17, 1989 [SE] Sweden ................................ 8903868

[51] Int. Cl.$^6$ ............................................. A61F 13/15
[52] U.S. Cl. ............................. 604/385.1; 604/385.2; 604/386
[58] Field of Search ......................... 604/358, 378, 604/385.1, 385.2, 386, 387, 349, 350; 2/403

[56] References Cited

U.S. PATENT DOCUMENTS

| | | | |
|---|---|---|---|
| 3,517,666 | 6/1970 | Atlee ................................. | 2/403 X |
| 4,668,230 | 5/1987 | D'Amico et al. .................... | 604/385 |
| 4,681,577 | 7/1987 | Stern et al. ........................ | 604/378 |
| 4,710,187 | 12/1987 | Boland et al. ..................... | 604/385.2 |
| 4,898,594 | 2/1990 | Cottenden ......................... | 604/397 |
| 4,904,251 | 2/1990 | Igaue et al. ....................... | 604/385.2 |
| 4,944,735 | 7/1990 | Mokry .............................. | 604/385.2 |
| 5,032,121 | 7/1991 | Mokry .............................. | 604/385.2 |
| 5,037,417 | 8/1991 | Ternström et al. ................. | 604/385.2 |
| 5,074,853 | 12/1991 | Bryant .............................. | 604/385.2 X |
| 5,074,856 | 12/1991 | Coe et al. .......................... | 604/385.2 |
| 5,129,893 | 7/1992 | Thorén ............................. | 604/385.2 |

FOREIGN PATENT DOCUMENTS

| | | | |
|---|---|---|---|
| 0155515 | 9/1985 | European Pat. Off. ............ | 604/385.2 |
| 0167931 | 1/1986 | European Pat. Off. . | |
| 0350871 | 1/1990 | European Pat. Off. ............. | 604/358 |
| 450811 | 8/1987 | Sweden . | |
| WO79/00008 | 1/1979 | United Kingdom . | |
| WO86/05386 | 9/1986 | United Kingdom . | |
| 2182840 | 5/1987 | United Kingdom . | |
| 8606621 | 11/1986 | WIPO ................................. | 604/350 |
| 9107156 | 5/1991 | WIPO ................................. | 604/358 |
| 9215269 | 9/1992 | WIPO ................................. | 604/349 |

Primary Examiner—Mary Beth O. Jones
Attorney, Agent, or Firm—Burns, Doane, Swecker & Mathis

[57] ABSTRACT

A male incontinence guard includes an inner, liquid permeable casing layer; an outer, liquid impermeable casing layer; an absorbent pad having a first end and enclosed between said layers so as to include a first side edge on one side of said pad and a second side edge on an opposite side of said pad; said absorbent pad narrows at the first end; a first elastic device attached in a prestretched state to the inner casing layer and extends from the first end along at least a part of said first side edge; and a second elastic device attached in a prestretched state to the inner casing layer and extends from the first end along at least a part of said second side edge; said elastic devices arranged such that contraction of said elastic devices causes said inner casing layer at the first end of said pad to take a concave shape and said outer casing layer at said first end of said pad to take a convex shape. The absorbent pad is narrower than said inner and outer casing layers so that said absorbent pad does not extend into said side edges, and said elastic devices are attached between said inner and outer casing layers. The absorbent pad is substantially triangular in shape.

23 Claims, 2 Drawing Sheets

INCONTINENCE GUARD FOR MEN

This application is a continuation of application Ser. No. 07/855,042, filed as PCT/SE90/00744, Nov. 16, 1990, now abandoned.

BACKGROUND OF THE INVENTION

1. Field of the Invention

The present invention relates to a male incontinence guard intended for one-time use only and including an inner, liquid-permeable casing layer which is intended to lie closest to the wearer's body in use, an outer, liquid-impermeable casing layer, and an absorbent body or pad located between said casing layers.

2. Description of Related Art

Incontinence guards used hitherto have normally consisted of conventional diapers of substantially flat configuration, for instance of rectangular shape. Diapers, however, are intended to absorb both urine and faeces and are therefore not appropriate for use by persons who solely require a urine-collecting incontinence guard. The diaper must have a given width and absorbent material a given thickness in order to achieve satisfactory absorbency. Consequently, the diaper will occur a correspondingly large space betweed the thighs of the wearer, so as to cause discomfort, such as chafing for instance. Furthermore, there is a serious risk that urine will leak at the edges of the diaper when the diaper becomes saturated and is compressed between the wearer's thighs.

Large, bulky diapers are unacceptable to males who suffer from incontinence but who are otherwise not handicapped. In addition to being uncomfortable when worn, large, bulky diapers are not readily accommodated in conventional clothing.

Mild incontinence is a hidden handicap suffered by many people. A large group of such people is comprised of males with prostate trouble. Subsequent to undergoing prostate surgery, these men are normally troubled by drop-incontinence, which hitherto has resulted in psysic suffering, since no suitable guard is available.

Incontinence guards intended for men afflicted with mild incontinence are known per se. When worn, one such known guard has the form of a cone-shaped container which embraces the genital organs of the male wearer. One drawback with this known guard is that it is much too warm and fits much too tightly when worn, and is therewith uncomfortable to the wearer. A further drawback is that the guard is much too inflexible for comfort.

The Swedish Patent Specification No. SE 450 811 teaches a male incontinence guard which comprises an upper shield-like part which lies over the penis and scrotum of the wearer in use, and a lower part which, in use, curves inwardly beneath the penis and scrotum of the wearer without completely enclosing the same. The guard has a downwardly narrowing and basin-like configuration. This guard thus avoids tightly enclosing the organs of the wearer, which is naturally beneficial from the aspect of comfort.

The guard is formed from a flat blank, one end part of which comprises two flaps whose mutually adjacent edge lines depart from a common point on the guard.

The basin-like configuration is obtained by bringing the flaps to a position in which the edge lines overlap one another, and then joining the flaps in this region.

One drawback with an incontinence guard of this design resides in the complicated manufacturing procedures required by the different clipping and joining steps.

SUMMARY AND OBJECTS OF THE PRESENT INVENTION

The present invention provides an incontinence guard for males who suffer mild drop-incontinence, with which the drawbacks of the aforesaid incontinence guards are not found.

An inventive incontinence guard is characterized in that at least a first part of the absorbent pad intended to embrace, completely or partially, the wearer's scrotum in use, narrows towards the scrotum end of the absorbent pad, i.e. towards the free end of said first part of the absorbent pad; in that at least one elastic device is attached, in a prestretched state, to the inner casing layer and extends from the scrotum end along each of the side edges of the absorbent pad over at least a part of their length; and in that contraction of the elastic device or devices from its or their prestretched state imparts to the first part of the absorbent body a curved shape such that said part will be curved inwardly beneath the wearer's scrotum when the guard is worn.

This results in a compliable incontinence guard which can be worn comfortably. Due to the effect of the elastic devices, the guard will conform more readily to the wearer's genitals than the known guards. Absorbent sanitary products, such as male incontinence guards, must not fit too tightly, feel uncomfortable and be too confining, these requirements being far from unessential. For psychological reasons, the guard should not even be thought to be tightly confining and unpleasant by the presumptive user.

As a result of its construction, an inventive incontinence guard is both simple to manufacture and easy to handle by the user. Triangular absorption pads can be manufactured rationally from a continuous web of absorbent material, without material waste and complicated folding steps.

BRIEF DESCRIPTION OF THE DRAWINGS

The invention will now be described in more detail with reference to an exemplifying embodiment thereof illustrated in the accompanying drawings, in which.

DETAILED DESCRIPTION OF A PREFERRED EMBODIMENT

Figure 1:
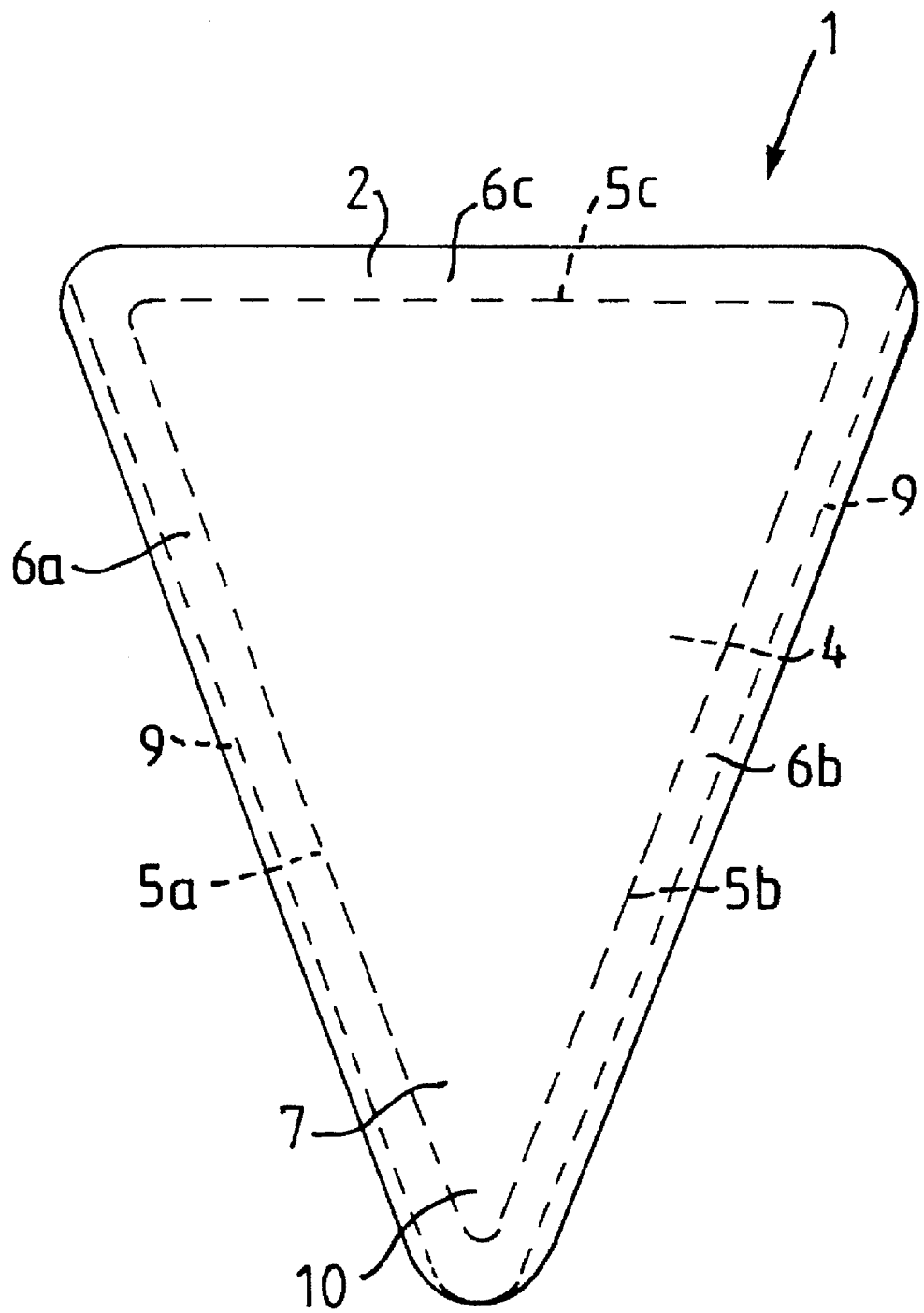
FIG. 1 illustrates one embodiment of an inventive guard and shows the guard extended with the side intended to lie against the wearer in use facing the viewer.
Figure 2:
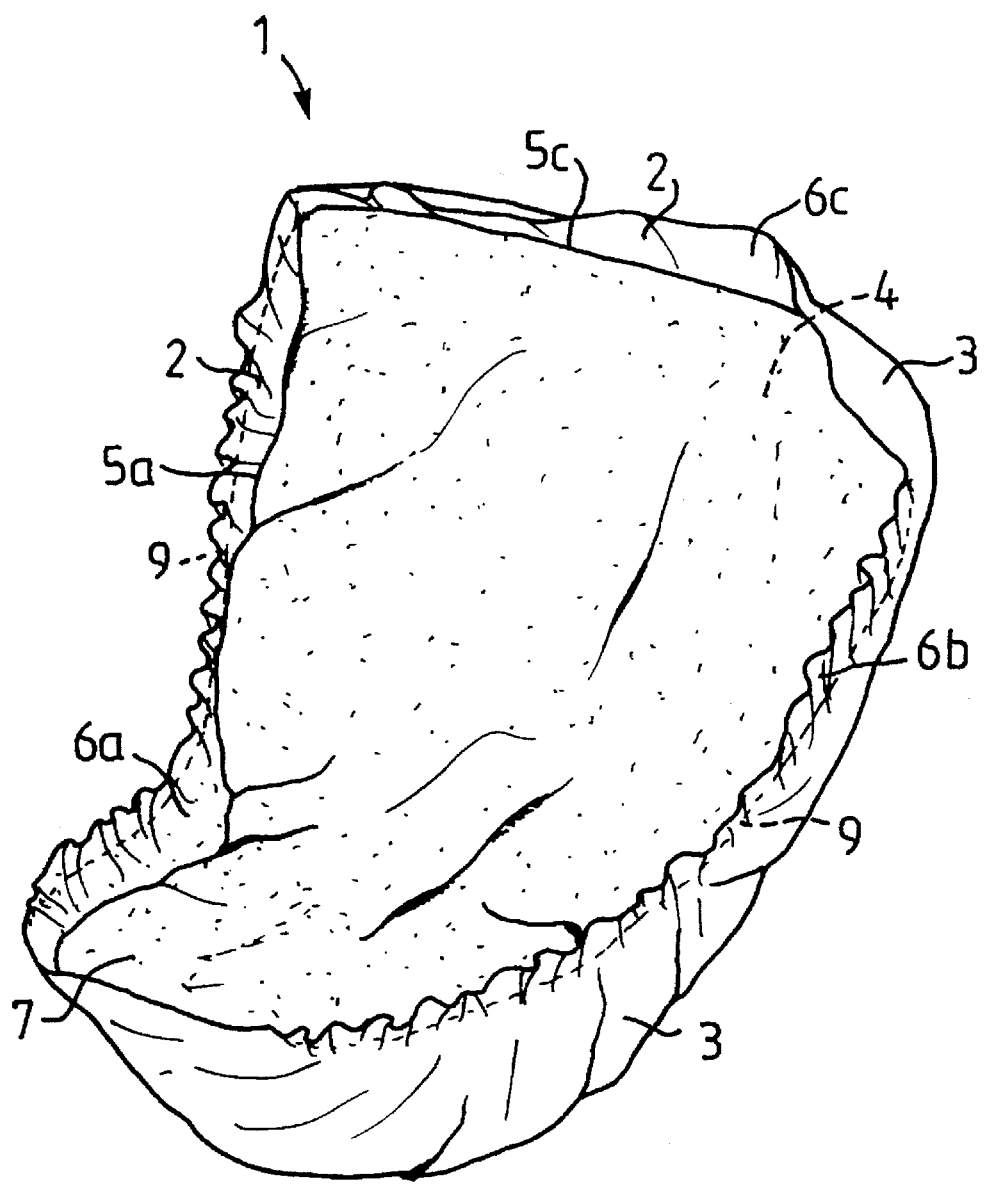
FIG. 2 is a perspective view of the guard illustrated in FIG. 1, and shows the elastication in its active state.

The incontinence guard 1 illustrated in FIGS. 1–2 comprises a liquid permeable layer 2, a liquid impermeable layer 3, and an absorbent pad 4 enclosed between the two layers 2 and 3. The pad 4 may comprise an absorbent fibre material, for instance fluff. If desired, the fluff can be admixed with other absorbent material, for instance so-called superabsorbent polymers, by which is meant polymers that are capable of absorbing liquid in quantities corresponding to many times the natural weight of the polymers. Other substances of a non-absorbent nature can be admixed in the absorbent pad, for instance melt fibres.

The absorbent pad may comprise either one absorbent layer or several absorbent layers, where the various layers may also comprise mutually different absorbent material. The absorbent pad 4 may have the shape of an isosceles triangle, with two edges 5a and 5b of mutually equal length and a third, shorter edge 5c.

The liquid permeable layer 2 is suitably made of non-woven material. Another conceivable material is perforated plastic. The liquid-impermable layer 3 may comprise a polyethylene or polypropylene plastic, or some other liquid impervious plastic. Another conceivable material is hydrophobized non-woven material. The outer layers 2 and 3 will preferably have the same thickness and shape, and both will project slightly beyond the edges 5a, 5b, 5c of the absorbent pad, such as to form side flaps 6a, 6b, 6c along which the layers 2 and 3 are mutually joined with the aid of a binder, for instance melt glue. The equally long edges 5a, 5b of the pad are therewith corresponded by side flaps 6a, 6b of mutually equal length, while the third edge 5c of the absorbent pad is corresponded by a third side flap 6c. The liquid impervious material in the asing 3 is preferably permeable to air and vapours.

Prestretched elastic devices 9 are attached in the side flaps 6a, 6b of mutually equal lengths. The elastic devices 9 may, for instance, have the form of elastic threads, bands or the like- The use of elastic foam material is also conceivable. The elastic devices are preferably glued to one or to both of the outer layers 2, 3. The elastic devices may be placed at any desired distance from the edges 5a, 5b, and the sid flaps 6a, 6b, 6c can have any desired size.

FIG. 1 illustrates the incontinence guard in an extended or outwardly stretched form, i.e. with the elastic devices in a prestretched state, whereas FIG. 2 illustrates the guard in the form in which it is used, i.e. with the elastic devices in a contracted state. Shortening of the elastic devices by contraction is permitted by curving of the absorbent pad 4. The local resistance of the pad to bending about axes parallel with the edge 5c decreases towards the end 10, and consequently the pad 4 will bend or curve more pronouncedly in the region nearest the end 10 than in parts more distal therefrom. As will be seen from FIG. 2, the elastic devices 9 generate a curved, container-like part 7 which is intended to embrace the scrotum of the wearer in use, either completely or partially. Due to bending or curvature of the absorbent pad, pleating of the casing materials caused by the elastic devices will cause the side flaps 6a, 6b to be upstanding in relation to the absorbent pad.

The elastic devices may be prestressed to the same or different degree within different parts of the side flaps 6a, 6b. Naturally, different degrees of elastic pretensioning can be considered, depending on the curvature desired and also on the desired size of the incontinence guard.

According to one preferred embodiment of the invention, the elastic devices are attached in the side flaps 6a, 6b in spaced relationship with the edges 5a, 5b of the absorbent pad. As a result of this arrangement, the elastic devices 9 lift-up the side flaps 6a, 6b so as to form leakage-preventing barriers. Furthermore, the side flaps can be utilized in a simple and practical fashion when putting on the guard. When putting on the guard, the guard is first twisted so as to curve in the opposite direction to that intended when the guard is worn, whereafter the guard is gripped with the fingers of one hand in the region of the pointed end 10, in one region of the side flaps 6a, 6b between the elastic devices 9 and the edges 5a, 5b of the absorbent pad, whereafter the guard is then twisted into position over the wearer's genitals, with the aid of the elastication.

Although not preferred, the elastic devices may alternatively be placed over the absorbent pad 4. In this case, the side flaps 6a, 6b are not raised by the elastic devices to form barriers and contraction of the elastic devices is permitted by pleating of the liquid permeable casing layer.

The invention shall not be considered to be limited to the aforedescribed exemplifying embodiments, since several modifications can be made within the scope of the following claims. For instance, the elastic devices 9 can be mutually joined at the end 10 and may consist of one single elastic thread.

Furthermore, the absorbent pad, similar to the incontinence guard, may have a narrowing form at least in that part which is intended to surround the scrotum. It will also be understood that triangles having rounded corners and triangles having non-linear edges are also conceivable. In order to enable.-the article to be gripped more readily when putting on the article, the absorbent pad may advantageously be provided with rounded recesses. This arrangement also results in higher sealing barriers, since the distance between the edge of the side flap and the edge of the absorbent pad increases when such recesses are provided.

It will also be understood that some form of absorbent material can also be included in the side flaps. In order to achieve a good elastic seal and enable the article to be twisted readily when putting on the article, the material used in the side flaps must be more flexible and bendable than the material used in the absorbent pad.

In one variant of the inventive article, it is conceivable to provide said article with cross-elastication, so that the absorbent pad will also bend around longitudinally extending axes.

Also conceivable is the use of casing material which will contract and is elastic subsequent to being heated, and to heat this elastication locally instead of using elastic threads and the like which must be held constantly stretched during manufacture of the guard.

We claim:

1. A male incontinence guard, comprising:

an inner, liquid permeable casing layer;

an outer, liquid impermeable casing layer;

an absorbent pad having a first end, said casing layers enclose said pad so as to include a first casing end and a second casing end opposite to said first casing end, a first side edge along one side of said pad and a second side edge along an opposite side of said pad;

said absorbent pad narrows at the first end;

a first elastic device attached in a prestretched state to the inner casing layer and extending from the first casing end along at least a part of said first side edge; and, a second elastic device attached in a prestretched state to the inner casing layer and extending from the first casing end along at least a part of said second side edge;

said elastic devices arranged such that contraction of said elastic devices causes a curvature such that said inner casing layer at the first casing end of said pad takes a concave shape and said outer casing layer at said first casing end of said pad takes a convex shape, the curvature being more pronounced at the first casing end and decreasing away from the first casing end along the side edges because local resistance of the pad to bending increases toward the second casing end.

2. The male incontinence guard of claim 1, wherein said absorbent pad is narrower than said inner and outer casing layers so that said absorbent pad does not extend into said side edges.

3. The male incontinence guard of claim 2, wherein said elastic devices are attached between said inner and outer casing layers.

4. The male incontinence guard of claim 1, wherein said absorbent pad is substantially triangular in shape.

5. The male incontinence guard of claim 1, wherein said first casing end forms a pouch.

6. The male incontinence guard of claim 1, wherein the pad is seamless.

7. The male incontinence guard of claim 6, wherein the curvature is more pronounced at the first casing end for accommodating a wearer's genitalia.

8. A male incontinence guard, comprising:

an inner, liquid permeable casing layer;

an outer, liquid impermeable casing layer;

an absorbent pad having a first end, said casing layers enclose said pad so as to include a first casing end enclosing the first end, a second casing end opposite to said first casing end, a first side edge along one side of said pad and a second side edge along an opposite side of said pad;

said absorbent pad narrows at the first end; and means attached to said inner casing layer at said first and second side edges for causing said first casing end to contract into a pouch in which said inner casing layer is in a concave shape and said outer casing layer is in a convex shape the contraction being more pronounced at the first casing end because local resistance of the pad to bending increases toward the second end for accommodating a wearer's genitalia and decreasing away from the first casing end along the side edges.

9. The male incontinence guard of claim 8, wherein said absorbent pad is narrower than said inner and outer casing layers so that said absorbent pad does not extend into said side edges.

10. The male incontinence guard of claim 9, wherein said means for causing said first casing end to contract are attached between said inner and outer casing layers.

11. The male incontinence guard of claim 8, wherein said absorbent pad is substantially triangular in shape.

12. A male incontinence guard, comprising:

an inner, liquid permeable casing layer;

an outer, liquid impermeable casing layer;

an absorbent pad having a first end, said casing layers enclose said pad so as to include a first casing end enclosing the first end, a second casing end opposite to said first casing end, a first side edge along one side of said pad and a second side edge along an opposite side of said pad;

said absorbent pad narrows at the first end; and means attached to said first and second side edges for causing said first casing end to contract into a pouch in which said inner casing layer is in a concave shape and said outer casing layer is in a convex shape the contraction being more pronounced at the first casing end because local resistance of the pad to bending increases toward the second end for accommodating a wearer's genitalia and decreasing away from the first casing end along the side edges.

13. The male incontinence guard of claim 12, wherein said means for causing said first casing end to contract is attached to said inner casing layer.

14. The male incontinence guard of claim 12, wherein said absorbent pad is narrower than said inner and outer casing layers so that said absorbent pad does not extend into said side edges.

15. The male incontinence guard of claim 14, wherein said causing means are attached between said inner and outer casing layers.

16. The male incontinence guard of claim 12, wherein said absorbent pad is substantially triangular in shape.

17. A male incontinence guard, comprising:

an inner, liquid permeable casing layer;

an outer, liquid impermeable casing layer;

an absorbent pad having a first end, said casing layers enclose said pad so as to include a first casing end enclosing the first end and a second casing end opposite to said first casing end, a first side edge along one side of said pad and a second side edge along an opposite side of said pad;

said absorbent pad narrows at the first end;

an elastic device attached in a prestretched state to the inner casing layer and extending along at least a part of said first side edge, around the first casing end, and along at least a part of said second side edge;

said elastic device arranged such that contraction of said elastic device causes a curvature such that said inner casing layer at the first end of said pad takes a concave shape and said outer casing layer at said first end of said pad takes a convex shape the curvature being more pronounced at the first casing end and decreasing from the first casing end along the side edges because local resistance of the pad to bending increases toward the second end.

18. The male incontinence guard of claim 17, wherein said absorbent pad is narrower than said inner and outer casing layers so that said absorbent pad does not extend into said side edges.

19. The male incontinence guard of claim 18, wherein said elastic device is attached between said inner and outer casing layers.

20. The male incontinence guard of claim 17, wherein said absorbent pad is substantially triangular in shape.

21. The male incontinence guard of claim 17, wherein said first casing end forms a pouch.

22. The male incontinence guard of claim 17, wherein the pad is seamless.

23. The male incontinence guard of claim 22, wherein the curvature is more pronounced at the first casing end for accommodating a wearer's genitalia.

* * * * *